United States Patent [19]

Yokotani

[11] Patent Number: 4,939,095
[45] Date of Patent: Jul. 3, 1990

[54] AUTOMATIC CHEMICAL ANALYZER

[75] Inventor: Noboru Yokotani, Ootawara, Japan

[73] Assignee: Kabushiki Kaisha Toshiba, Kawasaki, Japan

[21] Appl. No.: 370,079

[22] Filed: Jun. 22, 1989

Related U.S. Application Data

[63] Continuation of Ser. No. 117,345, Oct. 27, 1987, abandoned, which is a continuation of Ser. No. 831,874, Feb. 24, 1986, abandoned.

[30] Foreign Application Priority Data

Feb. 25, 1985 [JP] Japan ............................ 60-35911

[51] Int. Cl.⁵ ...................... G01N 21/13; G01N 35/02
[52] U.S. Cl. ........................................ 436/47; 422/64; 422/67
[58] Field of Search ................................. 422/63–67; 436/47; 356/39, 408, 428, 434

[56] References Cited

U.S. PATENT DOCUMENTS

| | | | |
|---|---|---|---|
| 4,276,051 | 6/1981 | Ginsberg et al. | 436/47 |
| 4,313,735 | 2/1982 | Yamashita et al. | 436/47 |
| 4,536,369 | 8/1985 | Sakurada et al. | 436/47 |
| 4,539,296 | 9/1985 | Manabe | 436/47 |
| 4,629,703 | 12/1986 | Offenheimer | 436/47 |

Primary Examiner—Michael S. Marcus
Attorney, Agent, or Firm—Oblon, Spivak, McClelland, Maier & Neustadt

[57] ABSTRACT

An automatic chemical analyzer has a compensation coefficient calculating section and a light-path-length-based compensating section. The calculating section obtains the ratio of the absorbancies measured of reaction cells filled with a sample of the known absorbancy to the absorbancy measured of each cell, thereby calculating compensation coefficients for the respective cells. The compensating section multiplies the absorbancies measured of the cells refilled with samples of different unknown absorbancies by the compensation coefficients calculated by the calculating section, thereby compensating the absorbancies for the light path lengths of the cells. The compensated absorbancies, i.e., the absorbancies of the samples, are used in analyzing the samples.

4 Claims, 3 Drawing Sheets

AUTOMATIC CHEMICAL ANALYZER

This application is a Continuation of application Ser. Number 117,345, filed on Oct. 27, 1987, now abandoned, which is a continuation of Ser. No. 831,874 filed Feb. 24, 1986 now abandoned.

BACKGROUND OF THE INVENTION

The present invention relates to an automatic chemical analyzer of direct measurement type, designed to subject a plurality of reaction cells, each containing a sample and a reagent, to photometric measurement to determine the absorbancy of the sample, thus analyzing the sample contained in the cell. More particularly, it relates to the technique of compensating for the measurement values for the difference among the light path lengths of the cells.

An automatic chemical analyzer uses a number of reaction cells shaped like a test tube. Each cell is filled with a sample (e.g., urine or serum) and a reagent reacting with a specific component of the sample. The cells are intermittently moved one after another to a position where the photometric measurement is carried out. Light is applied to each cell and passes through it. The light from the cell is separated by a diffraction grating into spectral components. The attenuation of the light component having a specific wavelength is measured, thus determining the content of a particular component of the sample.

To measure accurately the attenuation of the light caused by the samples, the difference in the light path lengths of the cells must be minimized. More specifically, the reaction cells must have substantially the same inner diameter. However, it is very difficult and it costs very much to manufacture such reaction cells. If provided with such cells, the analyzer will be greatly expensive. Therefore, the analyzers commercially available at present are designed with allowance for the difference ranging from ±0.17% to 0.33%.

As Lambert-Beer's law teaches, the difference in the light path length directly affects the accuracy of measurement. The difference ranging from ±0.17% to 0.33% cannot, therefore, be neglected, and it is desired that the influence of this difference on the measurement accuracy be minimized.

SUMMARY OF THE INVENTION

Accordingly, it is an object of the present invention to provide an automatic chemical analyzer which is not affected by the difference in the light path lengths of reaction cells and can thus analyze samples very accurately.

According to the invention, there is provided an automatic chemical analyzer comprising a calculating section for calculating a compensation coefficient from the absorbancy measured of a cell containing a sample of known absorbancy and the known absorbancy of the sample, and a compensating section for compensating the measured absorbancy for the light path length of the cell filled with the sample, in accordance with the compensation coefficient calculated by the calculating section.

The analyzer according to the invention is inexpensive, is free of the influence of the difference in the light path lengths of the reaction cells, and can thus analyze samples very accurately.

DETAILED DESCRIPTION OF THE PREFERRED EMBODIMENTS

First, the principle of the invention will be described. As is well known, Lambert-Beer's law is represented by the following equation:

$$\log (I_0/I) = K \cdot c \cdot l \tag{1}$$

where $\log (I_0/I)$ is the absorbancy of a sample. $I_0$ is the intensity of the light passed through pure water, I is the intensity of the light passed through the sample, K is a coefficient of absorbancy, c is the concentration of the sample, and l is the light path length (i.e., the thickness of the sample.

Let it be assumed that the absorbancy (Es) of a sample is known. When the standard light path length (ls) of reaction cells, the absorbancy coefficient (ks) of the sample, and the concentration (cs) of the sample are also known, Es is given as follows:

$$Es = ks \cdot cs \cdot ls \tag{2}$$

Suppose the sample is poured into a reaction cell. When the light path length of the cell is ls', the absorption (Es') of light occurring in the cell is given by the following equation:

$$Es' = ks \cdot cs \cdot ls' \tag{3}$$

Dividing Es of equation (2) by Es' of equation (3), we obtain:

$$Es/Es' = ls/ls' \tag{4}$$

Value ls/ls' can be used as coefficient a for compensating the absorbancy for length ls'. Hence, equation (4) reduces to:

$$a = Es/Es' \tag{5}$$

Suppose the reaction cell is emptied and filled with another sample whose absorbancy Ex is unknown. When the measured absorbancy of the other sample is found to be Ex', Ex can be obtained by multiplying Ex' by a.

That is:

$$Ex = a \cdot Ex' \tag{6}$$

In other words, Ex' can be compensated for the light path length ls' in accordance with coefficient a, thereby finding Ex, i.e., the correct absorbancy of the other sample.

An embodiment of the present invention will now be described with reference to the accompanying drawings.

Figure 1:
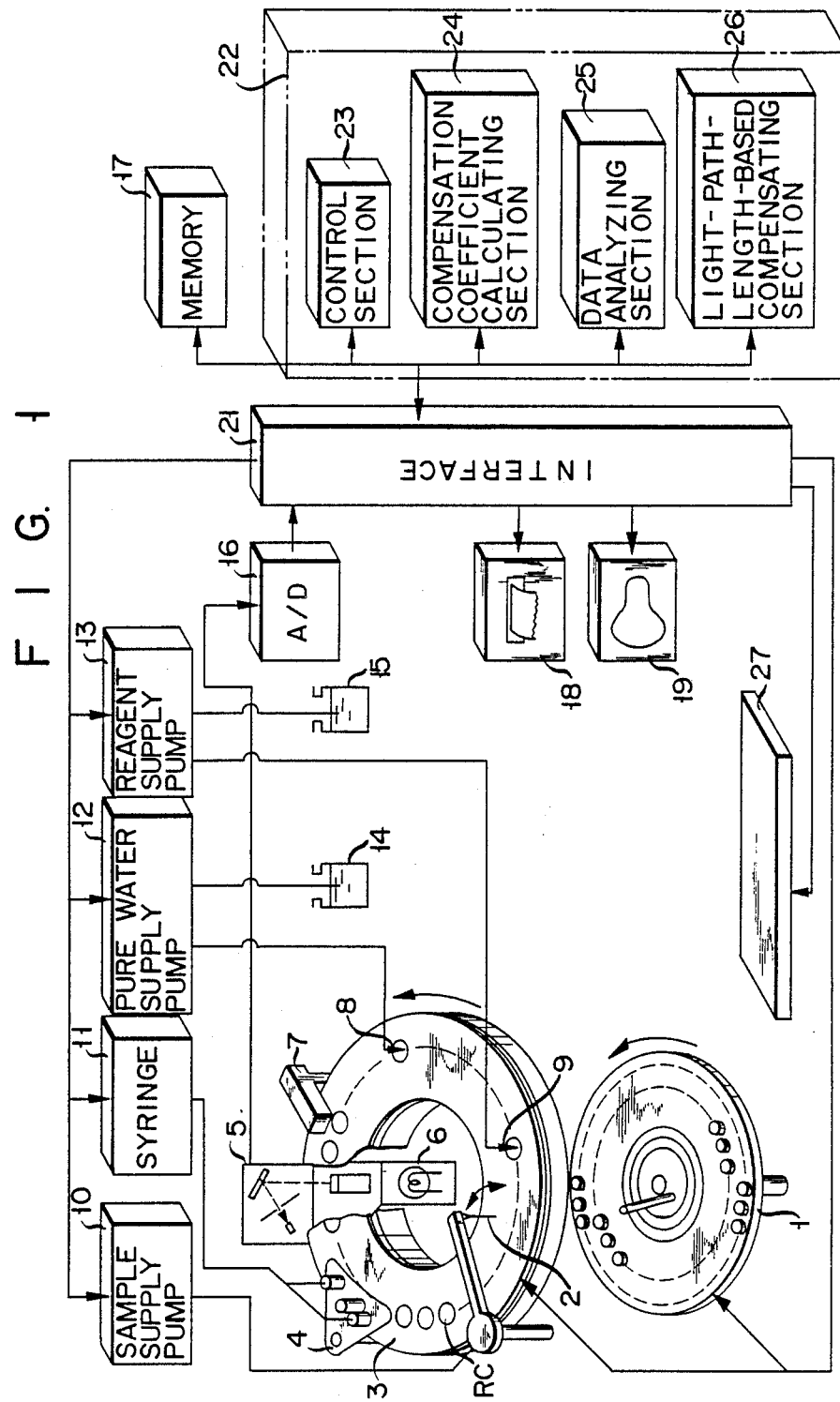
FIG. 1 is a block diagram of an automatic chemical analyzer according to the present invention.

As shown in FIG. 1, the embodiment, or an automatic chemical analyzer comprises first turntable 1, sample supply nozzle 2, second turntable 3, washing unit 4, photometer 5, light source 6, stirring unit 7, pure water supply nozzle 8, reagent supply nozzle 9, sample supply pump 10, syringe 11, pure water supply pump 12, reagent supply pump 13, pure water bottle 14, and a reagent bottle 15. It further comprises A/D converter 16, memory 17, printer 18, CRT display 19, interface 21, operation control unit 22 and console 27.

First turntable 1 has a number of holes arranged along the periphery. Similarly, second turntable 3 has a number of holes arranged in a circle along the periphery. The holes of turntable 1 are filled with a sample of known absorbancy and different samples of unknown absorbancies. Reaction cells RC are inserted in the holes of second turntable 3. Sample nozzle 2 sucks the samples from the holes of first turntable 1 and supplies them into cells RC. Washing circuit 4 is used to wash reaction cells RC. Light source 6 applies a light beam to cell RC brought to a prescribed position. Photometer 5 measures the intensity of the light passed through cell RC. Stirring unit 7 stirs the samples filled in cells RC so that the samples may be thoroughly mixed with the reagent supplied into cells RC from reagent bottle 15 by reagent supply pump 13. Pure water supply nozzle 8 supplies pure water into reaction cells RC. Sample supply pump 10 supplies samples into cells RC. Syringe 11 is used as a pump when washing unit 4 washes cells RC. Pure water supply pump 12 supplies pure water from bottle 14 to reaction cells RC. Reagent supply pump 13 supplies a reagent from bottle 15 to reaction cells RC.

Photometer 16 receives light from the reaction cell brought to a prescribed position and generates an analog signal representing the intensity of the light. A/D converter 16 converts the analog signal into a digital signal. The digital signal is supplied to operation control unit 22 through interface 21. Unit 22 performs various operations, thereby analyzing each sample. Unit 22 also supplies control data through interface 21, thus controlling some of the other components of the automatic chemical analyzer. Printer 18 receives and prints the results of the analysis. CRT display 19 is used to display the conditions of photometric measurement as well as the results of the analysis. Console 27 is operated to input various pieces of data including the conditions of photometric measurement.

Operation control unit 21 comprises control section 23, compensation coefficient calculating section 24, data analyzing section 25 and light-path-length-based compensating section 26. Control section 23 controls the pumps and turntable drives included in the automatic chemical analyzer. Section 24 performs the calculation expressed by equation (5). Namely, it computes the coefficient a for compensating the light path length of each cell RC filled with a sample of known absorbancy Es, from the absorbancy Es' measured of the cell and the known absorbancy Es of the sample. (The known absorbancy Es has been input by the operator from console 27.) Data analyzing section 25 calculates the absorbancy of cell RC containing the sample reacting with the reagent from the intensity of light measured by photometer 5, (Section 25 also analyzes the sample.) Compensating section 26 carries out the calculation represented by equation (6), thereby compensating absorbancy Ex' and obtaining absorbancy Ex corresponding to the value that could be obtained when the light passes a cell RC having the standard light path length.

More specifically, section 26 receives coefficient a, and compensates the absorbancy measured of the same cell RC containing another sample.

Figure 2:
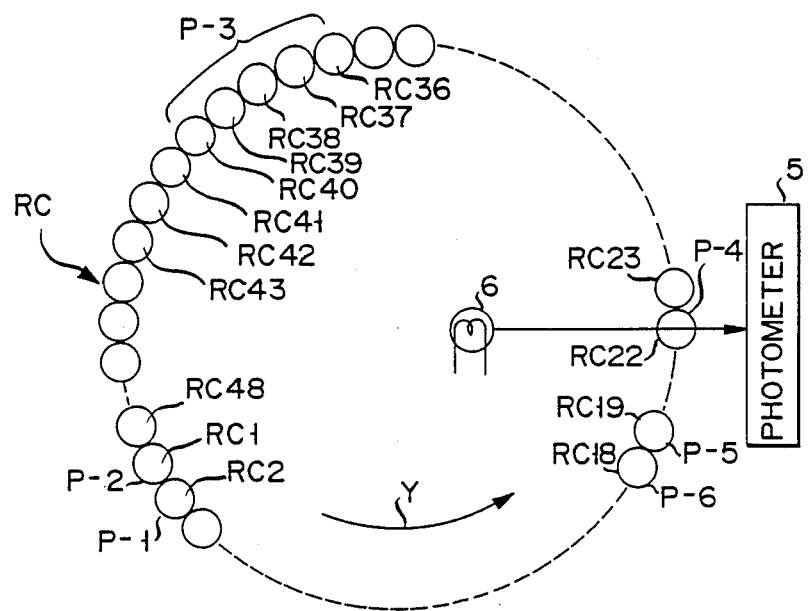
FIG. 2 schematically shows the positional relation between the reaction cell, on one hand, and photometer and a light source, on the other, all used in the automatic chemical analyzer.

The positional relation among the reaction cells mounted on second turntable 3 will be described with reference to FIG. 2. As shown in FIG. 2, forty-eight cells RC1-RC48 are arranged in a circle on second turntable 3. Second turntable 3 is intermittently rotated by a drive unit (not shown), and cells R1-R48 are moved in the direction of arrow Y. When each cell reaches positions P-1, P-2, P-3, P-4, P-5 and P-6, a reagent is poured into it, a sample is poured into it, it is washed, it is subjected to photometric measurement, its content is stirred, and pure water is poured into it, if necessary. Control section 23 controls the intermittent rotation of turntable 3, and hence the movement of cells R1-R48. Section 23 has the data showing where each cell exists.

Figure 3:
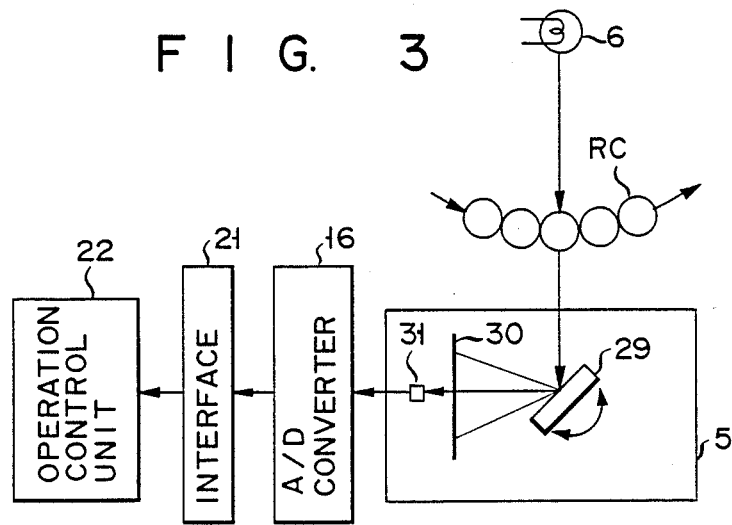
FIG. 3 schematically illustrates the internal structure of the photometer shown in FIG. 2.

As illustrated in FIG. 3, photometer 29 has a plate 30 with a diffraction grating 29, a slit 30 and a photodetector 31. Diffraction grating 29 separates the light, which has passed through reaction cells located at position R-4, into a plurality of monochromatic light beams. One of these beams is applied through slit 30 to photodetector 31. Photodetector 31 comprising, for example, a phototransistor, converts the monochromatic light beam into an electrical signal. The signal is input to operation control unit 22 through A/D converter 16 and interface 21.

Figure 4:
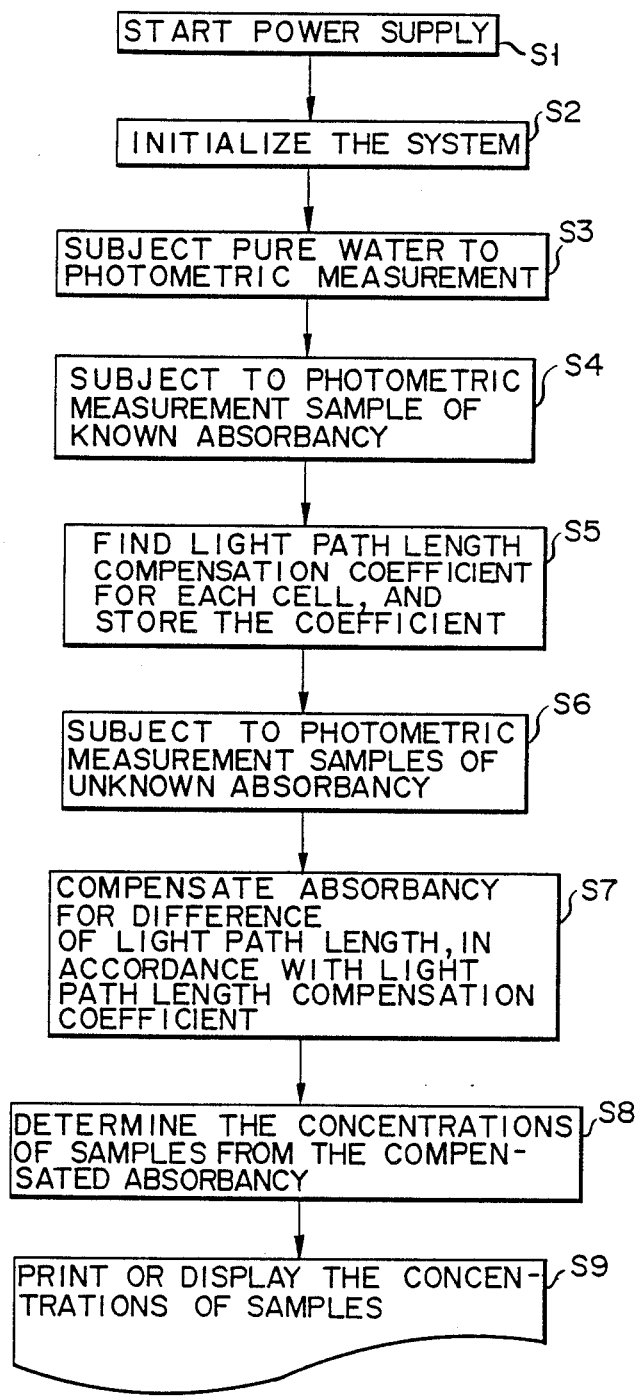
FIG. 4 is a flow chart explaining the operation of the analyzer shown in FIG. 1.

The operation of the automatic chemical analyzer will now be explained with reference to the flow chart of FIG. 4.

First, in step S1, the power supply switch of the analyzer is turned on. In step S2, the operator inputs various data, including measuring conditions, through console 27, thereby initializing the analyzer. Also in this step, the known absorbancy Es of a sample is input. These pieces of data are written through interface 21 in the specified storage area of memory 17.

In the next step, S3, reaction cells RC are filled with pure water and then subjected to photometric measurement, thereby obtaining $I_0$, i.e., the intensity of the light passed through each cell filled with pure water. More specifically, pump 12 supplies pure water from bottle 14 through nozzle 8 into each cell RC. Cell RC is brought to position P-4, and photometer 5 measures $I_0$. The data representing $I_0$ is written through A/D converter 16 and interface 21 in another storage area of memory 17.

The operation goes to step S4, in which the same cells are emptied. Pump 12 supplies the sample of the known absorbancy from a container mounted on first turntable 1 through nozzle 2 into cells RC. Each cell RC is brought to position P-4, and photometer 5 measures I, the intensity of the light passed through the cell filled with the sample. The data representing I is written through A/D converter 16 and interface 21 in data analyzing section 25. Data representing $I_0$ is read from memory 17 and supplied to section 25. Section 25 finds log $I_0/I$, i.e., absorbancy Es' measured of each cell RC. Data representative of Es' is input to section 24. Section 24 calculates, from Es' and Es, coefficient a for compensating the absorbancy of the sample filled in cell RS for the light path length ls' of cell RS. In step 5, the coefficients a thus calculated are different for reaction cells RC1-RC48. They are stored in the specified storage area of memory 17, and the numbers of the cells are also stored in the same area, in association with the coefficients.

After the coefficients a for all reaction cells RC1-RC48 have been calculated and written in memory 17, the operation advances to step S6. In step S6, the photometric measurement is carried out on the samples of unknown absorbancies, filled in reaction cells RC1-RC48. More specifically, syringe 11 is automatically operated, washing the reaction cells with pure water and, if necessary, with a detergent. Sample supply pump 10 supplies the samples from the containers mounted on first turntable 1 into cleaned cells RC1-RC48 through sample supply nozzle 2. Further, reagent supply pump 13 supplies a reagent from reagent bottle 15 into cells RC1-RC48 through reagent supply nozzle 9. The cells are brought to position P-5 one after another as second turntable 3 intermittently rotates in the direction of arrow Y (FIG. 2). Their contents are thus stirred by stirring unit 7 provided at position P-5. Cells RC1-RC48 are then moved to position P-4 one after another. Light source 6 emits light, which passes through each cell brought to position P-4. Photometer 5 receives the light from each cell and outputs the data representing the intensity of the light. The data is input to operation control unit 22 through A/D converter 16 and interface 21. Hence, the pieces of data representing the intensities I of the light beams passing through all cells RC1-RC48 are written in section 22 and supplied to data analyzing section 25. Section 25 calculates absorbancies Ex' for the samples filled in cells CR1-CR48, by processing the intensity data together with the intensity data $I_0$ (for pure water). Absorbancies Ex's are stored in a specified area of memory 17.

Coefficients a, which have been obtained in step S5, are read from memory 17 and input to light-path-length-based compensating section 26. In step S7, section 26 performs the calculation expressed by equation (6), thereby compensating the absorbancy Ex' also read from memory 17. As a result, absorbance Ex which could be measured if a cell having the standard light path length and filled with the sample were subjected to the photometric measurement. The data representing Ex is input to data analyzing section 25. In step S8, section 25 calculates the concentration of the sample from the input data representing Ex, in the same way as in the conventional automatic chemical analyzer. Hence, the concentrations of the samples are obtained. Then, the operation advances to step S9, in which the pieces of data representing the concentrations of the samples filled in cells RC1-RC48 and other pieces of data are supplied to printer 18 and CRT difference through interface 21, whereby printer 18 prints the concentrations and the other date, and display 19 displays them.

As described above, in the analyzer of the present invention, the sample of the known absorbancy Es is filled in clean reaction cells. Light source 6 applies light to these cells, and photometer 5 detects the intensities of the light beams from these cells, thereby measuring the absorbancies Es'. From the relation between known absorbancy Es and measured Es', section 24 calculates a coefficient a for compensating the absorbancy Es' for the light path length ls' of each cell. The cells are then washed and cleaned. Samples of unknown absorbancies are poured into the cleaned cells. Each cell is subjected to the photometric measurement, whereby absorbancy Ex' of the sample is measured. Absorbancy Ex' is compensated for ls', in accordance with coefficient a, thereby obtaining correct absorbancy Ex of the sample. Therefore, the analyzer of the invention can accurately determine the properties of samples, such as the concentrations, in spite of the unavoidable difference in light path length among the reaction cells. Hence, the analyzer of the invention does not require so high a precision of the cells as the conventional analyzer does.

The present invention is not limited to the above embodiment. Various changes and modifications can be made within the scope of the invention. For example, coefficients a for all reaction cells can be calculated at any time during the operation of the analyzer, not necessarily before the cells containing samples of unknown absorbancies are subjected to photometric measurement. Once the coefficients have been obtained and stored in memory 17, they need not be calculated again as long as the same reaction cells are used. Since the absorbancy "log ($I_0/I$)" of each sample can be expressed as "log $I_0$−log I," it can be calculated by a logarithm amplifier connected to the input of A/D converter 16, not by operation control unit 22.

What is claimed is:

1. An absorbancy-measuring method for employment in an automatic chemical analyzer wherein a plurality of reaction cells each having a light path length which may vary from a standard light path length are filled with a sample and a reagent and are subjected to photometric measurement, thereby measuring the absorbancies of the samples, said method comprising:
    a first step of subjecting reaction cells filled with a light absorbing liquid sample of known absorbancy to a photometric measurement using a photometer, thereby measuring the absorbancies of the cells filled with the sample;
    a second step of calculating compensation coefficients for the respective cells, on the basis of a ratio of known absorbancy to light through the standard light path length of the sample and the absorbancies measured of the cells in the first step;
    a third step of reusing the reaction cells of the first step by replacing the light absorbing liquid sample of known absorbancy with liquid samples of unknown absorbancy, thereby measuring the absorbancies of the cells filled with said samples of unknown absorbancies; and
    a fourth step of compensating the absorbancies measured in the third step for variations in the light path lengths of the cells from the standard light path by multiplying the absorbancies measured in the third step by respective compensation coefficients calculated in the second step.

2. A method according to claim 1, further comprising the step of storing the compensation coefficient calculated in the second step for the reaction cells.

3. An automatic chemical analyzer comprising:
    at least one reaction cell having an interior space defining a light path length through said at least one reaction cell, said light path defining a distance which may vary from a predetermined standard light path by an unknown amount;
    first supply means for supplying a known light absorbing liquid reference sample having a known light absorbancy to said at least one reaction cell;
    a single photometric means for directing light through said at least one reaction cell containing said reference sample supplied thereto by said first supply means, for measuring the amount of light absorbed by said at least one reaction cell containing said reference sample to produce a corresponding first absorbancy signal;

coefficient calculating means for calculating a correction coefficient for said at least one reaction cell based on the ratio of the known absorbancy of said known reference sample of light passed through a reaction cell having the standard light path length and the first absorbancy signal produced by said single photometric means, said correction coefficient being indicative of the amount of variation of the light path light length of the at least one reaction cell from the standard light path length;

memory means for storing said correction coefficient;

second supply means for supplying, subsequent to storing of said correction coefficient in said memory means, a mixture including at least one reagent and one sample to said at least one reaction cell, said mixture having an unknown absorbancy;

said single photometric means directing light through said reaction cell containing said mixture of unknown absorbancy supplied to said at least one reaction cell by said second supplying means, and measuring the amount of light absorbed by said at least one reaction cell containing said mixture of unknown absorbancy to produce a corresponding second absorbancy signal;

compensating means for multiplying said second absorbancy signal by said correction coefficient to produce a third absorbancy signal corresponding to the absorbancy of said mixture of unknown absorbancy in relation to said standard light path; and analyzing means for analyzing the properties of said mixture based on the compensated third absorbancy signal.

4. An automatic chemical analyzer according to claim 3, comprising:

plural reaction cells, wherein a respective correction coefficient is calculated and stored for each reaction cell and is used by said compensating means to compensate each respective second absorbancy signal to produce a corresponding respective third absorbancy signal.

* * * * *